(12) United States Patent
Sanborn

(10) Patent No.: US 7,420,067 B2
(45) Date of Patent: Sep. 2, 2008

(54) PROCESS FOR THE PRODUCTION OF ANHYDROSUGAR ALCOHOLS

(75) Inventor: Alexandra J. Sanborn, Lincoln, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 11/716,277

(22) Filed: Mar. 9, 2007

(65) Prior Publication Data

US 2007/0213544 A1 Sep. 13, 2007

Related U.S. Application Data

(60) Provisional application No. 60/780,907, filed on Mar. 9, 2006.

(51) Int. Cl.
C07D 307/93 (2006.01)
C07D 493/00 (2006.01)

(52) U.S. Cl. ...................... 549/465; 549/464

(58) Field of Classification Search .............. 549/465, 549/464
See application file for complete search history.

(56) References Cited

U.S. PATENT DOCUMENTS

| | | | |
|---|---|---|---|
| 3,160,641 A | 12/1964 | Hartmann | |
| 3,454,603 A | 7/1969 | Hartmann | |
| 4,297,290 A | 10/1981 | Stockburger | |
| 4,408,061 A | 10/1983 | Salzburg et al. | |
| 4,506,086 A | 3/1985 | Salzburg et al. | |
| 4,564,692 A | 1/1986 | Feldmann et al. | |
| 4,861,513 A | 8/1989 | Lueders et al. | |
| 6,818,781 B2 * | 11/2004 | Bhatia | 549/465 |
| 2002/0002291 A1 | 1/2002 | Bhatia | |
| 2002/0052516 A1 | 5/2002 | Moore et al. | |

FOREIGN PATENT DOCUMENTS

| | | |
|---|---|---|
| DE | 488 602 | 12/1929 |
| GB | 600870 | 4/1948 |
| WO | WO 00/14081 | 3/2000 |
| WO | WO 02/36598 A1 | 5/2002 |

OTHER PUBLICATIONS

Bahaluyan, D. et al., "Chiral polyesters with azobenzene moieties in the main chain, synthesis and evaluation of nonlinear optical properties", J. Mater. Chem 9:1425-1429, Royal Society of Chemistry (Jul. 1999).

Bock, K. et al., "Acid Catalyzed Dehydration of Alditols. Part I. D-Glucitol and D-Mannitol," Acta Chem. Scand. 35:441-449, Nordic Chemical Societies (1981).

Duclos, A. et al., "A Simple Conversion of Polyols into Anhydroalditols," Synthesis 10:1087-10980, Georg Thieme Verlag (1984).

Wiggins, L.F., "Anhydrides of the Penitols and Hexitols" Adv. Carb. Chem., pp. 191-228, Imperial College of Tropical Agriculture (1950).

Fleche, G. et al., "Isosorbide. Preparation, Properties and Chemistry," Starch 38:26-30, VCH Verlagsgesellschaft mbH (1985).

Goodwin, G. et al., "Preparation of bicyclic hexitol anhydrides by using acidic cation-exchange resin in a binary solvent. 13C-NMR spectroscopy confirms configuration inversion in chloride displacement of methanosulfunate in isomannide and isosorbide derivatives," Carb. Res. 79:133-141, Elsevier Scientific Publishing Company (1980).

Koch, H. et al., "New Industrial Products from Starch", Starch 40:128-129, Wiley-VCH (1988).

Marr, A. et al. "Synthesis and structure of 1,4:3,6-dianhydro-2-O-p-tosyl-D mannitol," J. Chem. Crystal. 27:161-166, Plenum Publishing Corporation (1997).

Stoss, P. et al., "1,4:3,6-Dianhydrohexitols," Adv. Carbohydr. Chem. Biochem. 49:93-173, Academic Press (1991).

Wiggins, L.F. "The Anhydrides of Polyhydric Alcohols. Part I. The Constitutition of isoMannide" J. Chem. Soc. 4-6, American Chemical Society (1945).

Supplementary European Search Report for EP 04 81 0609 dated Sep. 25, 2007.

Barker, Robert, "Conversion of Acyclic Carbohydrates into Tetrahydrofuran Derivatives, Acid-Catalyzed Dehydration of Hexitols", The Journal of Organic Chemistry, Feb. 1970, pp. 461-464, vol. 35, No. 2.

Hudson, B.G., et al., "The Conversion of Acyclic Carbohydrates to Tetrahydrofuran Derivatives, The Acid-Catalyzed Dehydration of Tetritols and Pentitols", Conversion of Acyclic Carbohydrates, Nov. 1967, vol. 32, pp. 3650-3658.

* cited by examiner

*Primary Examiner*—D. Margaret Seaman
*Assistant Examiner*—Nizal S Chandrakumar
(74) *Attorney, Agent, or Firm*—Buchanan Ingersoll & Rooney PC; Craig G. Cochenour; Duane A. Stewart, III

(57) ABSTRACT

A process is provided for the preparation of anhydrosugar alcohols. The process involves heating a sugar alcohol or a monoanhydrosugar alcohol starting material in the presence of an acid catalyst and under pressure. Optionally the resulting product is purified. Very high purities are achieved, without necessitating the use of organic solvents in the process.

22 Claims, 1 Drawing Sheet

PROCESS FOR THE PRODUCTION OF ANHYDROSUGAR ALCOHOLS

CROSS-REFERENCE TO RELATED APPLICATIONS

This Application claims the benefit of priority to pending U.S. Provisional Patent Application Ser. No. 60/780,907, filed on Mar. 9, 2006, entitled "Process for the Production Of Anhydrosugar Alcohols", and having the same named inventor, namely, Alexandra J. Sanborn. U.S. Provisional Patent Application Ser. No. 60/780,907 is incorporated by reference into this Application as if fully rewritten herein.

BACKGROUND OF THE INVENTION

1. Field of the Invention

The present invention relates to the production of anhydrosugar alcohols, also known as anhydroalditols or, in some cases, anhydrohexitols. More particularly, the present invention relates to a process for the production of anhydrosugar alcohols from sugar alcohol or monoanhydrosugar alcohol starting materials using elevated temperature and pressure.

2. Related Art

The chemical formation of closed-ring organic molecules has posed many issues for structural organic chemists. This has been particularly true with regard to synthetic reactions involving sugars and polyols, the acid dehydration of which leads to internal anhydro compounds (mono- and dianhydro products). Fleche and Huchette, Staerke 38:26-30 (1985) (hereby incorporated by reference in its entirety).

The earliest work in this area was done on 1,4:3,6-dianhydro-D-mannitol by Faucommier in 1884. Only sporadic work followed until the 1940's and 1950's, when intensive work was done on all possible isomers of 1,4:3,6-dianhydrohexitols. Stoss and Hemmer, Adv. Carbohydrate Chem. and Biochem. 93-173 (1991) (hereby incorporated by reference in its entirety). Since then a large body of chemical literature has developed in this area.

The 1,5:3,6-dianhydrohexitols belong to the so-called "biomass-derived substances," obtainable from natural products. Therefore, these compounds are classified as "regenerable resources." Furthermore, 1,4:3,6-dianhydrohexitols, such as isosorbide, can be used as starting materials and intermediates in various organic synthetic reaction schemes. For example, isosorbide is useful in the formation of numerous pharmaceutical compounds, in food production, cosmetic production, plastic and polymer production, and in other industrial uses such as in the production of polyurethane, polycarbonate, polyesters, and polyamides. Stoss and Hemmer, 1991. Examples of specific compounds in which isosorbide is used are isosorbide dimethyl ether, which is useful as an industrial solvent, a pharmaceutical additive, and in personal care products, and isosorbide dinitrate, which is useful as a medication to relieve the pain of angina attacks or reduce the number of such attacks by improving blood flow to the heart.

Of the known isohexides, isosorbide is considered to be that of the highest importance. Stoss and Hemmer (1991) describe putative steps leading from D-glucitol (also referred to in the art as sorbitol) to isosorbide. Acidic media are generally used for dehydrating the sugar alcohol substrate. Especially to enhance the yield and to avoid side reactions, certain modifications of the reaction conditions have been employed over the years, with various impacts on yield of isosorbide product. Stoss and Hemmer (1991).

Several processes for the production of anhydrosugar alcohols (including isohexides such as isosorbide) have been reported. For example, PCT application number PCT/US99/00537 (WO 00/14081), discloses collecting methods and a continuous production method with recycling of organic solvent. Most methods involve the use of concentrated acids and organic solvents. Goodwin et al., Carbohydrate Res. 79:133-141 (1980) have disclosed a method involving the use of acidic-cation-exchange resin in place of concentrated, corrosive acids, but with low yield of isosorbide product. An alternative is the supersaturation-based method, as disclosed in U.S. Pat. No. 4,564,692 (Feldmann, et al., Jan. 14, 1986). However, a need continues in the art for a process for production of very pure isosorbide, at reasonable yields. The above-cited references are hereby incorporated by reference in their entireties.

BRIEF SUMMARY OF THE INVENTION

The present invention relates to a process for the preparation of anhydrosugar alcohols from sugar alcohol or monoanhydrosugar alcohol starting materials using elevated pressure and elevated temperature.

In accordance with one aspect of the present invention, there is provided a process for producing an anhydrosugar alcohol comprising heating a pentitol or hexitol sugar alcohol or monanhydrosugar alcohol starting material, with or without solvent or catalyst, at an elevated temperature and pressure for a length of time (dependent on reaction conditions) sufficient to provide an anhydrosugar alcohol. The starting material may be heated, for example, until it is molten. The solvent that is added or excluded may be an organic solvent or an inorganic solvent. Following preparation, the anhydrosugar alcohol produced by a process of the invention may be purified. Purification may be accomplished, for example, by use of a film evaporator.

DETAILED DESCRIPTION OF THE INVENTION

Figure 1:
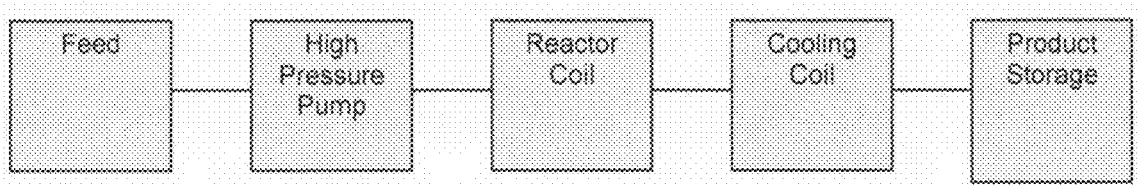
FIG. 1 is a flow chart showing a continuous reactor process as taught herein. The reactor vessel may be, for example, but is not limited to a pipe, tube, or wire.

In one aspect, the invention provides a process for producing an anhydrosugar alcohol comprising heating a pentitol or hexitol sugar alcohol or monoanhydrosugar alcohol starting material under elevated pressure until molten, with or without an organic solvent and with or without a catalyst, until the pentitol or hexitol sugar alcohol starting material has yielded an anhydrosugar alcohol.

In a further aspect, the acid catalyst a solid acid catalyst.

In a further aspect, the starting material used in the process is mixed with water to form a starting material solution.

In a further aspect, the solid acid catalyst is an inorganic ion exchange material selected from the group consisting of acidic ion exchange resins and acidic zeolite powders.

In a further aspect, the solid acid catalyst is an acidic ion exchange resin. In another embodiment, the acidic ion exchange resin is selected from the group consisting of AG50W-X12, Amberlyst 35, Amberlyst 15, RCP21H, and Dowex 50W×4. In another embodiment, the acidic ion exchange resin is Amberlyst 35. The acidic ion exchange resin may also be a sulfonated divinylbenzene/styrene copolymer acidic ion exchange resin.

In a further embodiment, the solid acid catalyst is an acidic zeolite powder. In one embodiment, the acidic zeolite powder is selected from the group consisting of CBV 3024, 5534G, T-2665, T-4480, and CS331-3. The solid acid catalyst may be a calcined zeolite.

In a further embodiment, the acid catalyst is a soluble acid catalyst. In one embodiment, the soluble acid catalyst is selected from sulfuric acid, phosphoric acid, p-toluenesulfonic acid, and p-methanesulfonic acid.

In a further embodiment the catalyst is present in an amount between about 0.10 equivalents of starting material to about 0.4 equivalents of starting material by weight. In a further embodiment the catalyst is present in an amount of about 0.20 equivalents of starting material by weight.

In a further embodiment, the production of an anhydrosugar alcohol is followed by purification comprising recrystallization of the anhydrosugar alcohol. In another embodiment, the recrystallization is a melt recrystallization. In another embodiment, the recrystallization is a solvent recrystallization. In one embodiment, the solvent recrystallization comprises heating said anhydrosugar alcohol with a solvent followed by gradual cooling at a rate of from about 8° C. to about 12° C. per minute. In one embodiment, the solvent recrystallization is performed with acetone as the solvent.

In a further embodiment, the purification further comprises a solvent wash followed by filtration. In another embodiment, the solvent wash is performed with a solvent which, for example, comprises methanol, acetone, ethyl acetate, and/or ethanol. In a preferred embodiment, the solvent wash is performed with acetone.

In a further embodiment, the purification further comprises distillation of the anhydrosugar alcohol mixture in a second film evaporator. In another embodiment, the second film evaporator is a wiped film evaporator. In another embodiment, the distillation in the second film evaporator is performed under the same temperature and pressure conditions as the distillation in the first film evaporator.

In a further embodiment, the process further comprises purification of the product anhydrosugar alcohol by centrifugation. In another embodiment, the process further comprises separation of the anhydrosugar alcohol by filtration.

In a further embodiment, the sugar alcohol or monoanhydrosugar alcohol starting material is selected from arabinitol, ribitol, sorbitol, mannitol, galactitol, iditol, erythritol, threitol, and mixtures thereof. In a preferred embodiment, the sugar alcohol or monoanhydrosugar alcohol starting material is sorbitol. In another preferred embodiment, the sugar alcohol or monoanhydrosugar alcohol starting material is mannitol.

In a further embodiment, the anhydrosugar alcohol is a dianhydrohexitol. In one embodiment, the dianhydrohexitol is isosorbide. In a further embodiment of the invention, the process produces a monoanhydrohexitol, sorbitan, also known as sorbitol anhydride.

In one embodiment of the invention, dehydration is performed at a temperature of from about 150° C. to about 350° C. In a further embodiment, dehydration is performed at a temperature of from about 200° C. to about 300° C. In another embodiment, the dehydration is performed at a temperature of from about 210° C. to about 290° C. In another embodiment, the dehydration is performed at a temperature of from about 215° C. to about 280° C. In another embodiment, the dehydration is performed at a temperature of from about 230° C. to about 270° C. In another embodiment, the dehydration is performed at a temperature of from about 240° C. to about 260° C.

In a preferred embodiment of the invention, the dehydration is performed at a temperature of about 280° C. This temperature is particularly suitable for conversion of sorbitol to isosorbide. Those skilled in the art will recognize, with the benefit of this disclosure, that necessary and/or optimal temperature for the reaction of the invention will vary with selected pressure. Use of certain catalysts, for instance, ion exchange resins, may dictate that the reaction be conducted at a lower temperature (for instance, at about 150° C.), resulting in a limited rate per amount of catalyst.

In a further embodiment, the dehydration is performed at an elevated pressure of from about 300 psi to about 2000 psi. In another embodiment, the dehydration is performed at an elevated pressure of from about 800 psi to about 1200 psi. In another embodiment, the dehydration is performed at a pressure of about 1000 psi. In a yet still further embodiment, the dehydration is performed at a pressure of about 1200 psi.

In a further embodiment including purification by distillation, the distillation in the first film evaporator is performed at a vapor temperature of from about 120° C. to about 190° C. and a pot temperature of at least the distilling point of the dehydrated anhydrosugar alcohol. In another embodiment, the distillation in the first film evaporator is performed at a vapor temperature of from about 160° C. to about 180° C. and a pot temperature of at least the distilling point of the dehydrated anhydrosugar alcohol. In another embodiment, the distillation in the first film evaporator is performed at a vapor temperature of from about 165° C. to about 170° C. and a pot temperature of at least the distilling point of the dehydrated anhydrosugar alcohol. In another embodiment, the distillation in the film evaporator is performed at a vapor temperature of about 170° C. and a pot temperature of at least the distilling point of the dehydrated anhydrosugar alcohol. The purification may preferably occur under normal atmospheric pressure or a vacuum, though those skilled in the art will recognize that an elevated pressure may also be used.

In a further embodiment including a purification step, the distillation in the first film evaporator is performed at a vacuum pressure of from about 0.00019 psi to about 0.76 psi. In another embodiment, the distillation in the first film evaporator is performed at a vacuum pressure of from about 0.0019 psi to about 0.19 psi. In another embodiment, the distillation in the first film evaporator is performed at a vacuum pressure of from about 0.019 psi to about 0.19 psi.

In one embodiment, the invention provides a process for producing an anhydrosugar alcohol comprising: (a) heating a pentitol or hexitol sugar alcohol or monoanhydrosugar alcohol starting material under elevated pressure until molten; (b) dehydrating the molten starting material in the presence of a solid acid catalyst to form an anhydrosugar alcohol mixture; (c) distilling the anhydrosugar alcohol mixture in a first film evaporator to produce a first anhydrosugar alcohol distillate; and (d) further purifying the anhydrosugar alcohol from the first anhydrosugar alcohol distillate.

In a further embodiment, the first film evaporator is a wiped film evaporator.

In a further embodiment, the further purification of the first anhydrosugar distillate comprises distillation of the first anhydrosugar alcohol distillate in a second film evaporator. In a further embodiment, the second film evaporator is a wiped film evaporator.

In a further embodiment, the further purification of the first anhydrosugar distillate comprises solvent recrystallization of the first anhydrosugar alcohol distillate. In another embodiment, the further purification of the first anhydrosugar distillate comprises melt recrystallization of the first anhydrosugar alcohol distillate. In another embodiment, the further purification of the first anhydrosugar distillate comprises a solvent wash followed by a filtration.

In a further embodiment including purification, the distillation in the first film evaporator is performed at a vapor temperature of from about 165° C. to about 170° C. and a pot temperature of at least the distilling point of the dehydrated anhydrosugar alcohol.

In a further embodiment, the distillation in the first film evaporator is performed at a vacuum pressure of from about 0.019 psi to about 0.19 psi.

In a further embodiment, the sugar alcohol or monoanhydrosugar alcohol starting material is sorbitol.

In a further embodiment, the anhydrosugar alcohol is isosorbide.

In a further embodiment, the solid acid catalyst is an acidic ion exchange resin. In another embodiment, the acidic ion exchange resin is Amberlyst 35 (Rohm & Haas). In another embodiment, the solid acid catalyst is a zeolite.

Starting Materials

Typical sugar alcohols, for example pentitols and hexitols, are suitable for use as starting materials in the process of the invention. As used herein, "pentitol" refers to a sugar alcohol or monoanhydrosugar alcohol having five carbon atoms (e.g., ribitol). As used herein, "hexitol" refers to a sugar alcohol or monoanhydrosugar alcohol having six carbon atoms (e.g., sorbitol or mannitol). The starting materials can include sugar alcohols or monoanhydrosugar alcohols, or a mixture of such sugar alcohols or monoanhydrosugar alcohols. Examples of starting materials include, but are not limited to, arabinitol, ribitol, glucitol (also referred to in the art as sorbitol, and referred to herein as sorbitol), mannitol (also known as manna sugar or mannite), galactitol (dulcitol), iditol, erythritol, threitol, and the like. Sorbitol is a particularly preferred starting material because it is readily available and because pure isosorbide (also known as dianhydrosorbitol) is very useful in a number of chemical and pharmaceutical applications. Sorbitol is commercially available in a 70% aqueous solution (Archer-Daniels-Midland Company) making it a preferred form of starting material for industrial use.

The process of the invention may also produce sorbitan, also known as sorbitol anhydride. Sorbitol esters are reportedly useful in cleaners and detergents, as polymer additives, in the textile industry as emulsifiers, as wetting agents, and as viscosity modifiers. Interest in sorbitan has also been expressed in the gel capsule industry.

In an initial step of a process of the present invention, the selected starting material may be combined with a solvent in a vessel capable of withstanding the enhanced temperatures and pressures of the invention. Such a solvent may be, for example, water. In another embodiment, a starting material solution (including or not including a catalyst as described below) may be transferred at a measured rate through a heated, pressurized tube or tubes for a period of time necessary to produce a desired yield (and constant or near-constant throughput) of product.

In a still further embodiment of the invention, a mixture of starting material and water may be subjected to microwave irradiation in which pressures suitable for the invention are also applied. Elevated pressures may be applied by placing the reactants in a sealed pressure reactor vessel prior to insertion in the microwave reactor. As with the other embodiments of the invention, pressure and/or temperature may be varied to produce difference amounts of the final product or of any desired intermediate.

Catalysts and Dehydration.

A catalyst that will facilitate the dehydration of the sugar alcohol may be added to the starting material solution. Typically the catalysts used to facilitate the dehydration of sugar alcohols are acid catalysts. The classes of acid catalysts useful in the practice of the present invention include, but are not limited to, soluble acids, acidic ion exchange resins, and inorganic ion exchange materials. Reusable or recyclable catalysts are preferred for use in the reaction, as they provide for increased efficiency, and economic and industrial feasibility. As used herein, the term "recyclable catalyst" refers to a catalyst which is not irreversibly expended as a result of the reaction. In other words, the catalyst may be used again.

Solid acid catalysts often comprise a solid material which has been functionalized to impart acid groups that are catalytically active. Solid acid catalysts may have a broad range of composition, porosity, density, type of acid groups and distribution of acid groups. Solid acid catalysts may be recovered and reused, optionally with a treatment to regenerate any activity that may have been lost in use. Some solid acid catalysts that may be used in the disclosed process include, but are not limited to, ion-exchange resins, inorganic ion exchange materials, Lewis acids, clays, and molecular sieves.

Soluble acids. In some embodiments, the acid catalyst of the present invention comprises a soluble acid. Soluble acids including, but not limited to, sulfuric acid, phosphoric acid, p-toluenesulfonic acid, and p-methanesulfonic acid are preferred for use in the present invention. One of skill in the art would recognize that other soluble acids with similar properties may be useful in the present invention although not specifically listed here.

Inorganic ion exchange materials. Zeolites are inorganic ion exchange materials. In some embodiments, the acid catalyst of the present invention comprises a zeolite, specifically an acidic zeolite, and more specifically, a type H-ZSM-5 zeolite. Preferred acid zeolites include H—Y zeolite, H-Mordenite zeolite, H-beta zeolite, and DA-Y zeolite. Examples of zeolites that are useful in the practice of the present invention include, but are not limited to, CBV 3024 or CBV 5534G (both available from Zeolyst International), T-2665, T-4480 and/or CS331-3 (the latter three available from United Catalysis, Inc.), and the like. One of skill in the art would recognize that other zeolites with similar properties may be useful in the present invention although not specifically listed here. Calcined zeolites are particularly preferred in the practice of the invention, especially for the production of isosorbide from sorbitol. One way to prepare a calcined zeolite is, for example, to take a zeolite as described above and heat it at a temperature of between about 300° C. to about 600° C. for about 2 hours. Calcined zeolites may also be purchased commercially. Sulfated metal oxide catalysts are those that comprise a mixture of metal ions, or a single metal ion, capable of being sulfated to produce a strongly acidic surface. A preferred sulfated metal oxide catalyst is sulfated zirconia. Calcination is generally required to activate sulfated zirconia.

Acidic Ion Exchange Resins. In some embodiments, the acid catalyst of the present invention comprises an acidic ion exchange resin. The acidic ion exchange resin may be, for example, a sulfonated divinylbenzene/styrene co-polymer acidic ion exchange resin. Examples of acidic ion exchange resins useful in the practice of the present invention include, but are not limited to, AG50W-X12 from BioRad Laboratories, Amberlyst 15 or Amberlyst 35 from Rohm & Haas, RCP21H from Mitsubishi Chemical Corp., Lewatit S2328, Lewatit K2431, Lewatit S2568, Lewatit K2629 from Bayer Corporation, and Dowex 50Wx 5 (Dow Chemical Co.). The sulfonated divinylbenzene/styrene co-polymer acidic ion exchange resin Amberlyst 35 is a particularly preferred resin in the practice of the present invention, specifically for the production of isosorbide from sorbitol. One of skill in the art would recognize that other acidic ion exchange resins with similar properties may be useful in the present invention although not specifically listed here.

The amount of catalyst used will vary depending upon the reaction conditions and starting material, as those of skill in the art will appreciate with the benefit of this disclosure, but will generally be on the order of from about 0.10 equivalents to about 1.0 equivalents by weight, about 0.10 to about 0.35 equivalents by weight, about 0.10 to about 0.30 equivalents by weight, about 0.10 to about 0.25 equivalents by weight, about 0.15 to about 0.35 equivalents by weight, about 0.15 to about 0.30 equivalents by weight, or about 0.15 to about 0.25 equivalents by weight. A preferred amount of catalyst is about 0.2 equivalents by weight.

It is possible to perform one or more dehydrations of the starting sugar alcohol during the reaction, producing, for example, a mono- or dianhydrosugar alcohol. The reaction may also be controlled so as to produce a combination of mono- and dianhydrosugar alcohols by adjusting either the reaction conditions or the starting materials, which as those of skill in the art will appreciate, could contain both sugar alcohols and monoanhydrosugar alcohols.

The dehydration in the presence of the catalyst can be carried out under pressure, at elevated temperatures, and with stirring of the reaction mixture. The pressure can range over a pressure of from about 300 psi to about 2000 psi, with preferred pressures of from about 800 psi to about 1500 psi. As a specific example, a preferred pressure for the dehydration step in the process of the present invention in which isosorbide is made from sorbitol is from about 800 psi to about 1200 psi.

A range of temperatures are suitable for use in the invention. In one embodiment of the invention, dehydration is performed at a temperature of from about 150° C. to about 350° C. In a further embodiment, dehydration is performed at a temperature of from about 200° C. to about 300° C. In another embodiment, the dehydration is performed at a temperature of from about 210° C. to about 290° C. In another embodiment, the dehydration is performed at a temperature of from about 215° C. to about 280° C. In another embodiment, the dehydration is performed at a temperature of from about 230° C. to about 270° C. In another embodiment, the dehydration is performed at a temperature of from about 240° C. to about 260° C. In the production of isosorbide from sorbitol, for example, the dehydration can be carried out for approximately 30 minutes, with constant stirring, at a temperature of about 280° C.

It will, of course, be appreciated by those of skill in the art that, in a process such as that of the present invention that involves application of both elevated temperature and pressure, the specific parameters of the process, including the time it takes to carry certain steps to completion, will vary depending upon the temperatures and pressures used. For example, the inventor has determined that higher pressure and temperature levels lead to a faster reaction time; however, excessively long reaction times may lead to degradation and polymerization of the desired product. An additional variable is the selected starting material, which will have a particular melting point and optimal pressure for reaction. This is equally true for the purification processes described below. However, given the disclosure presented herein, it is within the level of skill in the art to optimize the process parameters of the invention for a particular application. This can be done with only a few preliminary experiments, and without undue experimentation, in light of the instant disclosure.

Purification

Following the dehydration procedure, the product may be neutralized and water removed by rotary evaporation. Neutralization may be accomplished by, for example, addition of sodium hydroxide. Following the dehydration procedure, the resultant anhydrosugar alcohol mixture may be purified. In one embodiment, a vacuum distillation is used for purification. In a more specific embodiment, the vacuum distillation is performed using a film evaporator, specifically a wiped film evaporator. One example of a wiped film evaporator apparatus that is useful in the present invention is a vertical agitated thin-film processor. Advantages of using a wiped film evaporator include handling of viscous solutions, improved product purity, and low residence time, which leads to a reduction or elimination of product degradation. Specifically with respect to production of isosorbide from sorbitol, use of a wiped film evaporator provides approximately 80% yield on distillation, negligible water loss during distillation (which results in reduced polymerization), and provides for further recovery of isosorbide and sorbitan from the residue. The distillation process results in a first anhydrosugar alcohol distillate.

As noted above, the parameters for vacuum distillation will vary depending upon the material to be purified, and the temperature and pressure, as will be appreciated by those of ordinary skill in the art. The pot temperature will depend upon the temperature at which the material to be purified distills (i.e., the distillation point), which, again, will depend on the vacuum applied in the system. For example, in the case of isosorbide, a range of vapor temperatures of from about 140° C. to about 190° C. is preferred; more preferred is from about 160° C. to about 170° C.; even more preferred is from about 165° C. to about 170° C. The vacuum pressure can be from about $9.6 \times 10^{-4}$ psi to about 0.77 psi; preferably about 0.019 psi. For example, and specifically with regard to vacuum distillation of isosorbide, a vacuum pressure of about 019 psi, a pot temperature of about 180° C., and a vapor temperature of from about 160° C. to about 170° C. are most preferred.

Alternative purification methods of the anhydrosugar alcohol mixture such as filtration of the anhydrosugar alcohol mixture, or the addition of activated carbon with subsequent crystallization of the anhydrosugar alcohol mixture, are also useful in the present invention.

In one embodiment, to further purify and isolate the anhydrosugar alcohol, an anhydrosugar alcohol distillate is subjected to a second vacuum distillation, specifically in a film evaporator, and more specifically in a wiped film evaporator. The second wiped film evaporator can be of the same type as, or different than, the first wiped film evaporator. The conditions (e.g., vacuum pressure and temperature) of the second vacuum distillation can be the same as, or different than, the conditions of the first vacuum distillation, the parameters of which are described above. The use of two film evaporators allows for purification of anhydrosugar alcohols, specifically isosorbide, without the use of potentially harmful organic solvents.

In another aspect of the invention, to further purify and isolate the anhydrosugar alcohol, the first anhydrosugar alcohol distillate is subjected to melt crystallization. The recovered distillate product is heated until molten, and then cooled over time until the crystallization point is reached, but not so much that the material solidifies. In fact, a slurry-like consistency is preferred, so that the material can be centrifuged. As used herein, the term "slurry-like consistency" refers to recrystallized anhydrosugar alcohol distillate that is a mixture of liquid with several finely divided particles. The centrifugation is performed at a relatively high speed for a relatively short period of time to avoid solidification of the material, and also to avoid having the desired purified anhydrosugar alcohol end product be drawn off with the remaining impurities. For example, the centrifugation can be performed at about 3000 to about 4000 rpm for about 5 minutes. However, one of skill in the art will appreciate that the time of the centrifugation will vary depending on the amount of material to be purified. The resulting anhydrosugar alcohol product can be at least 98% pure, and in most cases will be greater than 99% pure (depending upon the solidity of the "slurry"). Alternatively, the first anhydrosugar alcohol distillate is subjected to solvent recrystallization in order to further purify and isolate the anhydrosugar alcohol. Solvents that are useful in the present invention include, but are not limited to, acetone, ethyl acetate, and low molecular weight alcohols such as ethanol and methanol.

In another embodiment, in order to further purify and isolate the anhydrosugar alcohol, the first anhydrosugar alcohol distillate can subjected to a solvent wash followed by filtration. Preferably, the solvents are cold, specifically at a temperature of about 0° C. to about 23° C. Solvents that are useful in the present invention include, but are not limited to, acetone, ethyl acetate, and low molecular weight alcohols such as ethanol and methanol. Filtration can be carried out be means that are well known in the art.

The present invention is described in further detail in the following non-limiting examples.

EXAMPLES

Example 1

Sorbitol (25.21 g) was dissolved in water (500 ml) and then transferred to a 1 L autoclave reactor vessel. The catalyst, MFI-40 (HZSM-5 zeolite, 5.02 g), was added. After flushing three times with hydrogen, pressure was set to 300 psi and the reactor was heated with stirring to 280° C. The pressure increased to 1100 psi with heating. Timing began when the reactor reached 280° C. After 30 minutes a 42.4% yield of isosorbide (calculated as mol isosorbide produced/mol starting sorbitol) was obtained.

Example 2

Sorbitol (37.78 g) was dissolved in water (500 ml) and transferred to a 1 L autoclave reactor vessel. The catalyst, calcined CBV 3024E (Zeolyst International, 7.55 g), was added and after flushing the reactor three times with hydrogen, pressure was set to 500 psi. The reactor was heated, with stirring, to 280° C., over a time period of about 30 to about 45 minutes. The pressure increased to 1200 psi over time. After 15 minutes at 280° C., the yield of isosorbide was 51.4%.

Example 3

Sorbitol (75.4 g) was dissolved in water (500 ml) and transferred to a 1 L autoclave reactor vessel. The catalyst, CBV 5524G (Zeolyst International, 15.10 g), was added and after flushing the reactor three times with hydrogen, pressure was set to 1000 psi. The reactor was allowed to heat to 280° C. with constant stirring (940 rpm). The pressure increased to 1150 psi over time. After 30 minutes at 280° C., the yield of isosorbide was 41.4%.

Example 4

Tables 1 through 8, below, detail the results of further additional experiments conducted according to the novel process of the invention. The experiments were conducted using the methods and apparatus as described in Example 1, with the reagent amounts as set forth in the table. The resulting amounts of isosorbide produced over time are also listed.

TABLE 1

| Reference # | Catalyst[1] | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 1-A | MFI-40 | 4:1 | 0 | room temp (rt) | 0 | 15700 | 0 | 100.0 | 0.0 |
| | | | 1 | 260 | 700 | 5900 | 2500 | 37.8 | 19.4 |
| | | | 3 | | | 4600 | 5200 | 29.3 | 40.3 |
| | | | 4 | | | 300 | 5800 | 1.9 | 45.0 |
| | | | 5 | | | 20 | 5700 | 0.1 | 44.2 |
| | | | 6 | | | 10 | 5900 | 0.1 | 45.7 |
| | | | 7 | | | 10 | 6100 | 0.1 | 47.3 |
| | | | 10½ | | | 0 | 6100 | 0.0 | 47.3 |
| | | | 28 | | | 0 | 6470 | 0.0 | 50.2 |
| 1-B | MFI-40 | 2:1 | 0 | rt | 0 | 16000 | 0 | 100.0 | 0.0 |
| | | | 1 | 254 | 600 | 2179 | 5154 | 13.6 | 39.6 |
| | | | 2 | 260 | 700 | 2232 | 6839 | 1.4 | 52.5 |
| | | | 3 | | | 0 | 7015 | 0.0 | 54.0 |
| | | | 5 | | | 0 | 7371 | 0.0 | 56.7 |
| | | | 8 | | | 0 | 7185 | 0.0 | 55.3 |
| | | | 14 | | | 0 | 7652 | 0.0 | 58.9 |
| | | | 19 | | | 0 | 7769 | 0.0 | 59.8 |
| 1-C | MFI-40 | 2:1 | 0 | rt | 0 | 15700 | 0 | 100.0 | 1.0 |
| | | | ½ | 280 | 900 | 1790 | 5510 | 11.4 | 42.7 |
| | | | 1 | | | 0 | 5960 | 0.0 | 46.2 |
| | | | 2½ | | | 0 | 4530 | 0.0 | 35.1 |
| | | | 3 | | | 0 | 4230 | 0.0 | 32.7 |
| | | | 4 | | | 0 | 3670 | 0.0 | 28.4 |
| | | | 5 | | | 0 | 3170 | 0.0 | 24.6 |
| | | | 6 | | | 0 | 2520 | 0.0 | 19.5 |

TABLE 1-continued

| Reference # | Catalyst[1] | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 1-D | MFI-40 | 1:1 | 0 | rt | 0 | 16000 | 0 | 100.0 | 0.0 |
| | | | ½ | 262 | 700 | 1700 | 5340 | 10.6 | 48.8 |
| | | | 1 | 260 | | 160 | 6350 | 0.1 | 49.8 |
| | | | 1½ | | | | 6470 | 0.0 | 46.5 |
| | | | 2 | | | | 6050 | 0.0 | 37.2 |
| | | | 4 | | | | 4840 | 0.0 | 32.3 |
| | | | 22½ | | | | 1630 | 0.0 | 12.5 |

TABLE 2

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 2-A | MFI-40 | 1:1 | 0 | rt | 0 | 16100 | 0 | 100.0 | 0.0 |
| | | | 1 | 250 | 700 | 2070 | 5470 | 12.9 | 39.8 |
| | | | 1¼ | | | 0 | 6220 | 0.0 | 45.2 |
| | | | 1½ | | | 0 | 6520 | 0.0 | 47.4 |
| | | | 1¾ | | | 0 | 6450 | 0.0 | 47.4 |
| | | | 2 | | | 0 | 6340 | 0.0 | 46.1 |
| | | | 2¼ | | | 0 | 6300 | 0.0 | 45.8 |
| | | | 2½ | | | 0 | 6070 | 0.0 | 44.1 |
| | | | 3 | | | 0 | 6020 | 0.0 | 43.8 |
| | | | 3½ | | | 0 | 5800 | 0.0 | 42.2 |
| 2-B | MFI-40 | 2:1 | 0 | rt | 0 | 16900 | 0 | 100.0 | 0.0 |
| | | | ¼ | 277 | 950 | 250 | 6120 | 1.5 | 43.9 |
| | | | ½ | 281 | 1000 | 0 | 5190 | 0.0 | 37.3 |
| | | | ¾ | 280 | | 0 | 5120 | 0.0 | 36.8 |
| | | | 1 | | | 0 | 4480 | 0.0 | 32.2 |
| | | | 1½ | | | 0 | 3560 | 0.0 | 25.6 |
| | | | 1¾ | | | 0 | 3190 | 0.0 | 22.9 |
| | | | 3¼ | | | 0 | 1670 | 0.0 | 12.0 |
| 2-C | MFI-40 | 3:1 | Starting soln | rt | 180 | 16500 | 180 | 100.0 | 1.3 |
| | | | 0 | 274 | 800 | 3170 | 840 | 19.2 | 6.2 |
| | | | ¼ | 273 | 850 | 1700 | 1380 | 10.3 | 10.1 |
| | | | ½ | 280 | 950 | 1000 | 4760 | 6.1 | 35.0 |
| | | | ¾ | 280 | 1000 | 170 | 5610 | 0.0 | 44.2 |
| | | | 1 | | | 0 | 6010 | 0.0 | 43.8 |
| | | | 1½ | | | 0 | 5830 | 0.0 | 42.9 |
| | | | 3 | | | 0 | 4850 | 0.0 | 35.7 |
| | | | 4 | | | 0 | 4520 | 0.0 | 33.3 |
| | | | 6 | | | | 3780 | 0.0 | 27.8 |
| 2-D | MFI-40 | 5:1 | Starting soln | rt | 0 | 47500 | 520 | 100.0 | 1.3 |
| | | | 0 | 282 | 1100 | 9500 | 11700 | 20.0 | 29.9 |
| | | | ½ | 280 | 1000 | 420 | 16600 | 1.0 | 42.4 |
| | | | 1 | | | 0 | 15600 | 0.0 | 39.8 |
| | | | 1¾ | | | 0 | 14500 | 0.0 | 37.0 |

TABLE 3

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 3-A | | | 4 | | | 0 | 12100 | 0.0 | 30.9 |
| | | | 6 | | | 0 | 11200 | 0.0 | 28.6 |
| | | | 7¾ | | | 0 | 9900 | 0.0 | 25.3 |
| 3-B | MFI-40 | 5:1 | Starting soln | rt | 0 | 74549 | 0 | 100.0 | 0.0 |
| | | | 0 | 280 | 1000 | 13955 | 18103 | 24.3 | 29.4 |
| | | | ¼ | 279 | 1100 | 792 | 25023 | 1.1 | 40.7 |
| | | | ½ | 280 | 1200 | 0 | 25760 | 0.0 | 42.0 |
| | | | 1 | | | 0 | 23255 | 0.0 | 37.9 |
| | | | 1½ | | | 0 | 22623 | 0.0 | 36.8 |
| | | | 1¾ | | | 0 | 22805 | 0.0 | 37.1 |

TABLE 3-continued

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| | | | 3½ | | | 0 | 19958 | 0.0 | 32.5 |
| | | | 4 | | | 0 | 19309 | 0.0 | 31.4 |
| | | | 5 | | | 0 | 18686 | 0.0 | 30.4 |
| | | | 6 | | | 0 | 18301 | 0.0 | 29.8 |
| 3-C | MFI-40 | 2:1 | 0 | rt | 0 | 16700 | 0 | 100.0 | 0.0 |
| | | | ¼ | 268 | 850 | 4370 | 3390 | 26.2 | 24.6 |
| | | | ½ | 270 | 850 | 1530 | 4740 | 9.2 | 34.4 |
| | | | ¾ | | | 450 | 5770 | 2.7 | 41.9 |
| | | | 1 | | | 140 | 6220 | 0.0 | 45.2 |
| | | | 1¼ | | | 0 | 6360 | 0.0 | 46.2 |
| | | | 1½ | | | 0 | 6220 | 0.0 | 45.2 |
| | | | 2¾ | | | 0 | 5640 | 0.0 | 41.0 |
| | | | 3½ | | | 0 | 5230 | 0.0 | 38.0 |
| | | | 4½ | | | 0 | 4770 | 0.0 | 34.7 |
| 3-D | CBV3024 | 5:1 | Starting soln | rt | 0 | 70424 | | 100.0 | 0.0 |
| | | | 0 | 260 | 800 | 9618 | 21291 | 13.7 | 37.2 |
| | | | 0 | 272 | 1000 | 1155 | 28039 | 1.6 | 49.1 |
| | | | ¼ | 279 | 1000 | 159 | 29330 | 0.2 | 51.4 |
| | | | ½ | 280 | 1100 | 0 | 26999 | 0.0 | 47.4 |
| | | | 1 | | 1100 | 138 | 24172 | 0.2 | 42.4 |
| | | | 3 | | 1200 | 0 | 18203 | 0.0 | 31.9 |
| | | | 4 | | | 0 | 15975 | 0.0 | 28.0 |
| | | | 5 | | | 0 | 15061 | 0.0 | 26.4 |

TABLE 4

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 4-A | CBV3024 | 5:1 | Starting soln | rt | 0 | 150488 | 55 | 100.0 | 0.0 |
| | | | 0 | 274 | 950 | 7303 | 43380 | 4.9 | 35.0 |
| | | | ¼ | 268 | 900 | 0 | 56093 | 0.0 | 45.2 |
| | | | ¾ | | | 0 | 54910 | 0.0 | 44.3 |
| | | | 1 | | | 0 | 53288 | 0.0 | 43.0 |
| | | | 1½ | | | 0 | 51816 | 0.0 | 41.8 |
| | | | 3 | | | 0 | 49663 | 0.0 | 40.0 |
| 4-B | CBV3024 | 5:1 | Starting soln | rt | 0 | 142650 | 50 | 100.0 | 0.0 |
| | | | 0 | 260 | 800 | 31751 | 34798 | 22.2 | 29.6 |
| | | | ¼ | | 800 | 4723 | 51465 | 3.3 | 43.8 |
| | | | ½ | | 900 | 0 | 56015 | 0.0 | 47.6 |
| | | | ¾ | | 950 | 0 | 55703 | 0.0 | 47.4 |
| | | | 1 | | 950 | 0 | 54833 | 0.0 | 46.6 |
| | | | 1½ | | 1000 | 0 | 54422 | 0.0 | 46.3 |
| | | | 2 | | 1000 | 0 | 53806 | 0.0 | 45.8 |
| | | | 3½ | | | 0 | 52468 | 0.0 | 44.6 |
| | | | 6 | | | 0 | 49773 | 0.0 | 42.3 |
| 4-C | CBV3024 | 10:1 | Starting soln | rt | 0 | 149602 | 0 | 100.0 | 0.0 |
| | | | 0 | 257 | 750 | 97632 | 7424 | 65.4 | 6.0 |
| | | | ¼ | 256 | 750 | 35226 | 31671 | 23.5 | 25.7 |
| | | | ½ | 260 | 800 | 9195 | 46832 | 6.1 | 38.0 |
| | | | ¾ | | 850 | 3069 | 52018 | 2.1 | 42.2 |
| | | | 1 | | 850 | 1311 | 55162 | 1.0 | 44.7 |
| | | | 1½ | | 900 | 561 | 55303 | 0.0 | 44.9 |
| | | | 1¾ | | | 384 | 56511 | 0.0 | 45.8 |
| | | | 3½ | | | 70 | 57863 | 0.0 | 46.9 |
| | | | 3¾ | | | 0 | 58888 | 0.0 | 47.8 |
| | | | 4½ | | | 0 | 58432 | 0.0 | 47.4 |
| | | | 6 | | | 0 | 57804 | 0.0 | 46.9 |
| | | | 6½ | | | 0 | 58467 | 0.0 | 47.4 |
| 4-D | CBV3024 | 5:1 | Starting soln | rt | 0 | 71833 | 0 | 100.0 | 0.0 |
| | | | 0 | 216 | 500 | 61444 | 627 | 85.0 | 1.1 |
| | | | ¼ | 275 | 900 | 478 | 25672 | 0.6 | 43.4 |

TABLE 5

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 5-A | CBV3024 | 5:1 | Starting soln | rt | 0 | 75309 | 44 | 100.0 | 0.0 |
| | | | 0 | 280 | 1100 | 32293 | 9430 | 42.9 | 15.2 |
| | | | ¼ | 274 | 1100 | 7864 | 19105 | 10.4 | 30.8 |
| | | | ½ | 280 | 1200 | 1002 | 24505 | 1.3 | 39.5 |
| | | | 1 | | | 31 | 25895 | 0.0 | 41.7 |
| | | | 1¾ | | | 0 | 25730 | 0.0 | 41.5 |
| | | | 3½ | | | 0 | 25199 | 0.0 | 40.6 |
| | | | 4¾ | | | 0 | 23840 | 0.0 | 38.4 |
| | | | 6½ | | | 0 | 21181 | 0.0 | 34.1 |
| 5-B | CBV5534G | 5:1 | Starting soln | rt | 0 | 146419 | 0 | 100.0 | 0.0 |
| | | | 0 | 234 | 600 | 123705 | 1272 | 84.5 | 1.0 |
| | | | 0 | 276 | 1000 | 24576 | 40449 | 16.8 | 33.5 |
| | | | ¼ | 277 | 1050 | 118 | 49982 | 0.0 | 41.4 |
| | | | ½ | 280 | 1050 | 0 | 48915 | 0.0 | 40.5 |
| | | | ¾ | | | 0 | 46947 | 0.0 | 38.9 |
| | | | 1 | | | 0 | 44115 | 0.0 | 36.6 |
| | | | 1½ | | | 0 | 42041 | 0.0 | 34.8 |
| | | | 2 | | | 0 | 38953 | 0.0 | 32.2 |
| | | | 3½ | | | 0 | 37849 | 0.0 | 31.2 |
| | | | 4 | | | 0 | 34301 | 0.0 | 28.4 |
| | | | 4¾ | | | 0 | 32535 | 0.0 | 27.0 |
| | | | 5½ | | | 0 | 31350 | 0.0 | 26.0 |
| 5-C | LZY-64 | 2:1 | 1½ | 250 | 600 | NT | 243 | NT | trace |
| | | | 2½ | | | | 790 | NT | trace |
| | | | 4½ | | | | 559 | NT | trace |
| | | | 5 | | | | 595 | NT | trace |
| 5-D | Na-6 | 2:1 | 0 | 260 | 700 | 15000 | 0 | 100.0 | 0.0 |
| | | | ½ | | | 9940 | 630 | 66.3 | 5.1 |
| | | | 1 | | | 8570 | 760 | 57.1 | 6.2 |
| | | | 1½ | | | 6860 | 1410 | 45.7 | 11.5 |
| | | | 3 | | | 2950 | 2380 | 24.0 | 19.3 |
| | | | 4 | | | 2350 | 2800 | 15.7 | 22.8 |
| | | | 6 | | | 1290 | 3410 | 8.6 | 27.7 |
| | | | 24 | | | 180 | 5000 | 1.2 | 41.0 |

TABLE 6

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 6-A | Na-6 | 1:1 | 0 | rt | 0 | 15700 | 0 | 100.0 | 0.0 |
| | | | 1 | 280 | 1000 | 1800 | 4240 | 11.5 | 30.8 |
| | | | 1¾ | | | 140 | 5660 | 0.9 | 43.7 |
| | | | 3 | | | 0 | 5560 | 0.0 | 43.0 |
| | | | 4 | | | 0 | 5540 | 0.0 | 42.8 |
| | | | 4½ | | | 0 | 5260 | 0.0 | 40.7 |
| | | | 5½ | | | 0 | 5460 | 0.0 | 42.2 |
| 6-B | SCM-8 | 2:1 | 0 | 249 | 550 | 15500 | 0 | 100.0 | 0.0 |
| | | | 1 | 260 | 700 | 11200 | 510 | 72.3 | 4.0 |
| | | | 1½ | | | 9910 | 690 | 63.9 | 8.4 |
| | | | 3½ | | | 7620 | 1320 | 49.2 | 10.3 |
| | | | 4 | | | 6690 | 1390 | 43.2 | 10.9 |
| | | | 6 | | | 5540 | 1850 | 35.7 | 14.5 |
| | | | 12 | | | 2170 | 3540 | 14.0 | 18.3 |
| | | | 29 | | | 2780 | 1860 | 17.9 | 13.4 |
| 6-C | LZY-84 | 2:1 | 0 | 251 | 600 | 15800 | 0 | 100.0 | 0.0 |
| | | | 1 | 260 | 700 | 14800 | 99.8 | 93.7 | 0.0 |
| | | | 1½ | | | 14100 | 64.6 | 91.0 | 0.0 |
| | | | 3½ | | | 13100 | 162 | 84.5 | 1.4 |
| | | | 5 | | | 11700 | 219 | 74.0 | 1.9 |
| | | | 6 | | | 12000 | 390 | 75.9 | 3.4 |
| | | | 12 | | | 10300 | 596 | 65.1 | 5.1 |
| | | | 29 | | | 6180 | 1060 | 39.1 | 9.1 |
| 6-D | CBV3024 | 5:1 | 0 | 223 | 900 | 119139 | 149 | | |
| | | | ¼ | 216 | 850 | 81282 | 7322 | | |
| | | | ½ | 221 | 850 | 50459 | 19271 | | |
| | | | ¾ | 220 | | 34878 | 26553 | | |

TABLE 6-continued

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| | | | 1 | | | 26959 | 31161 | | |
| | | | 1½ | | | 15146 | 39194 | | |
| | | | 2 | | | 9500 | 43662 | | |
| | | | 3¾ | | | 3488 | 51228 | | |
| | | | 4½ | | | 62 | 53377 | | |
| | | | 6½ | | | 0 | 55533 | 0.0 | 56.6 |

TABLE 7

| Reference # | Catalyst | Sorbitol: Catalyst | Time (h) | Temp (C.) | Pressure (psi) | Sorbitol (ppm) | Isosorbide (ppm) | Recovered Sorbitol (%) | Conversion to Isosorbide (%) |
|---|---|---|---|---|---|---|---|---|---|
| 7A | Sulfated zirconia | 5:1 | ¾ | | 1000 | 0 | 50255 | | |
| | | | 1 | | 1000 | 157 | 50187 | | |
| | | | 1½ | | 1050 | 0 | 44209 | | |
| 7B | T-2665 | 5:1 | Starting soln | rt | 0 | 129737 | 0 | 100.0 | 0.0 |
| | | | 0 | 271 | 800 | 25030 | 47390 | 19.3 | 44.3 |
| | | | 0 (after reaction conditions achieved) | 279 | 900 | 1543 | 39992 | 2.2 | 37.4 |
| | | | ¼ | 278 | 950 | 337 | 44666 | 0.5 | 41.2 |
| | | | ½B | | | 131 | 49054 | 0.2 | 45.9 |
| | | | ¾ | | | 0 | 43895 | 0.0 | 41.1 |
| | | | 1 | | | 183 | 34698 | 0.3 | 32.5 |
| | | | 1½ | | | 0 | 35256 | 0.0 | 33.0 |
| 7C | T-4480 | 5:1 | Starting soln | rt | 0 | 130425 | 967 | 100.0 | 0.0 |
| | | | ¼ | 279 | 950 | 35954 | 1295 | 1.8 | 33.4 |
| | | | ½ | 280 | 1050 | 24416 | 419 | 0.6 | 22.7 |
| | | | ¾ | 280 | 1050 | 19126 | 236 | 0.3 | 17.8 |
| | | | 1 | | 1050 | 21555 | 181 | 0.3 | 20.1 |
| | | | 1½ | | 1050 | 34383 | 323 | 0.5 | 32.0 |
| | | | 3 | | 1150 | 28281 | 209 | 0.3 | 26.3 |

[1]MFI-40 zeolite (SiO2/Al2O3 mole ratio = 40), CBV3024 zeolite (mole ratio = 30), CBV5534G zeolite (mole ratio = 50).

Example 6

Example 6 demonstrates the formation of sorbitan and isosorbide from sorbitol using a process of the invention. In test No. 8A 75 g of sorbitol was mixed with 15 g of calcined CS331-3 catalyst as described above and subjected to increased temperature using the method and apparatus described in Example 1, but with the parameters described in Table 8. After twenty hours of reaction at the given conditions, sorbitan was obtained in a yield of 57.6%, and isosorbide was obtained in a yield of 8.0%

Example 7

Example 7 demonstrates the formation of sorbitan and isosorbide from sorbitol. Concentrated sulfuric acid (0.20 mL) was added to a 70% sorbitol solution (50 g). The reaction was carried out in a sealed pressure reactor vessel at a pressure of about 130 psi. The vessel was introduced to the Milestone Microsynth microwave reactor for 30 minutes at 170° C. The final product comprised 50.4% sorbitan, 7.8% isosorbide, and 11.9% sorbitol.

TABLE 8

| # | Catalyst | Sorbitol:Catalyst | Time (h) | Temp (° C.) | Pressure (psi) | Sorbitol (ppm) | Sorbitan (ppm/%) | Isosorbide (ppm/%) | Recovered Sorbitol (%) |
|---|---|---|---|---|---|---|---|---|---|
| 8A | CS331-3 | 5:1 | starting sol'n | room temp. | 0 | 130835 | 513/0% | 0/0% | 100 |
| | | | 0 | 270 | 800 | 120585 | 9604/8.0% | 188/0.2% | 92.4 |
| | | | 0.25 | 282 | 1000 | 97565 | 29479/24.4% | 1556/1.4% | 74.7 |
| | | | 0.5 | 280 | 900 | 37104 | 22965/19.1% | 1755/1.6% | 28.4 |
| | | | 20+ | room temp. | 100 | 10468 | 69534/57.6% | 16555/8.0% | 15.4 |

Example 8

A sugar alcohol or monoanhydrosugar alcohol solution is pumped through a heated continuous coil reactor to form an anhydrosugar alcohol. A continuous coil reactor may be similar, for example, to the one shown in FIG. 1 of U.S. Pat. No. 2,735,792, incorporated by reference herein. The temperature and flow rate is controlled to produce high yields of an anhydrosugar alcohol. A second pass of a monoanhydrosugar alcohol containing solution through the heated coil generates higher yields of an anhydrosugar alcohol.

Having now fully described the present invention in detail by way of illustration and example for purposes of clarity of understanding, it will be apparent to one of ordinary skill in the art, with the benefit of this disclosure, that the invention can be performed by modifying or changing the invention with a wide and equivalent range of conditions, formulations and other parameters thereof. Furthermore, it will be apparent to the skilled practitioner with the benefit of this disclosure that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A process for the production of an anhydrosugar alcohol, comprising:
   (a) mixing a pentitol or hexitol sugar alcohol or monoanhydrosugar alcohol starting material with a solvent and an acidic catalyst to form a starting material solution, and, optionally, stirring said starting material solution;
   (b) heating said starting material solution to a temperature of about 150° C. to about 350° C.;
   (c) pressurizing said starting material solution to a pressure of about 130 psi to about 2000 psi; and
   (d) forming an anhydrosugar alcohol in the solution.

2. The process of claim 1, further comprising collecting said anhydrosugar alcohol.

3. The process of claim 1, including wherein said acidic catalyst is selected from the group consisting of at least one solid acid catalyst and at least one soluble acid catalyst.

4. The process of claim 1, including wherein said acidic catalyst is selected from the group consisting of sulfuric acid, phosphoric acid, p-toluenesulfonic acid, and p-methanesulfonic acid.

5. The process of claim 1, including wherein said acidic catalyst is an inorganic acid exchange material.

6. The process of claim 5, including wherein said inorganic acid exchange material is a zeolite.

7. The process of claim 6, including wherein said zeolite is a calcined zeolite.

8. The process of claim 6, including wherein said zeolite is selected from the group consisting of CBV 3024, CBV 5534G, T-2665, T-4480, and CS 331-3.

9. The process of claim 5, including wherein said inorganic acid exchange material is an acidic ion exchange resin.

10. The process of claim 9, including wherein said acidic ion exchange resin is selected from the group consisting of AG50W-X 12, Amberlyst 15, Amberlyst 35, Amberlyst 36, Amberlyst 131, Lewatit S2328, Amberlyst 35, Amberlyst 36, Amberlyst 15, Amberlyst 131, Lewatit S2328, Lewatit K2431, Lewatit S2568, Lewatit K2629, Dianion SK104, Dianion PK228, Dianion RCP160, and Relite RAD/F, RCP21H, and Dowex 50Wx 5.

11. The process of claim 9, including wherein said acidic ion exchange resin is a sulfonated divinylbenzene/styrene copolymer acidic ion exchange resin.

12. The process of claim 1, including wherein said acidic catalyst is present in an amount between about 0.10 equivalents to about 1.00 equivalents by weight of starting material.

13. The process of claim 1, including wherein said starting material solution is reacted at a pressure between about 300 psi to about 2000 psi.

14. The process of claim 1, including wherein said starting material solution is heated to a temperature selected from the group consisting of a temperature between about 200° C. to about 300° C., a temperature between about 210° C. to about 290° C., a temperature between about 215° C. to about 280° C., a temperature between about 230° C. to about 270° C., and a temperature between about 240° C. to about 260° C.

15. The process of claim 1, including wherein said heating and pressurizing steps are conducted under microwave irradiation.

16. The process of claim 1, including wherein said heating and pressurizing occur in at least one tube during a constant throughput of starting material.

17. The process of claim 1, wherein said starting material solution is heated to a temperature between about 150° C. to about 350° C. and pressurized to a temperature between about 300 psi to about 2000 psi.

18. The process of claim 4, wherein said starting material solution is heated to a temperature between about 150° C. to about 350° C. and pressurized to a temperature between about 300 psi to about 2000 psi.

19. The process of claim 6, wherein said starting material solution is heated to a temperature between about 150° C. to about 350° C. and pressurized to a pressure between about 300 psi to about 2000 psi.

20. The process of claim 15, wherein said starting material solution is heated to a temperature of about 170° C. and pressurized of about 130 psi.

21. The process of claim 1, including wherein said pentitol or hexitol sugar alcohol or monoanhydrosugar starting material is selected from the group consisting of arabinitol, ribitol, glucitol, mannitol, galactitol, iditol, erythritol, threitol, and mixtures thereof.

22. The process of claim 1, including wherein said hexitol sugar alcohol starting material is glucitol.

* * * * *